United States Patent

Patsch et al.

[11] Patent Number: 6,120,562
[45] Date of Patent: Sep. 19, 2000

[54] TRIAZINE DERIVATIVES AS FIXERS IN COLORING AND AS CROSS-LINKING AGENTS

[75] Inventors: Manfred Patsch, Wachenheim; Reinhold Krallmann, Weisenheim; Wolfgang Reuther, Heidelberg; Thomas Grösser, Ludwigshafen, all of Germany

[73] Assignee: BASF Aktiengesellschaft, Ludwigshafen, Germany

[21] Appl. No.: 09/147,047

[22] PCT Filed: Mar. 10, 1997

[86] PCT No.: PCT/EP97/01209

§ 371 Date: Sep. 25, 1998

§ 102(e) Date: Sep. 25, 1998

[87] PCT Pub. No.: WO97/35848

PCT Pub. Date: Oct. 2, 1997

[30] Foreign Application Priority Data

Mar. 25, 1996 [DE] Germany .......................... 196 11 668

[51] Int. Cl.$^7$ ...................... C07D 251/70; D06M 13/358
[52] U.S. Cl. .................. 8/541; 8/566; 8/673; 8/680; 544/196; 544/197; 544/198; 544/208; 544/209
[58] Field of Search .................... 544/196, 197, 544/198, 208, 209; 8/541, 566, 673, 680

[56] References Cited

U.S. PATENT DOCUMENTS

| 3,278,253 | 10/1966 | Weckler et al. | 544/196 |
|---|---|---|---|
| 3,400,121 | 9/1968 | Weckler et al. | 544/196 |
| 5,792,222 | 8/1998 | Adam et al. | 544/208 |

FOREIGN PATENT DOCUMENTS

| 0 175 225 | 3/1986 | European Pat. Off. . |
|---|---|---|
| 0 538 977 | 4/1993 | European Pat. Off. . |
| WO 94/29282 | 12/1994 | European Pat. Off. . |
| 0 682 019 | 11/1995 | European Pat. Off. . |
| 43 20 447 | 12/1994 | Germany . |
| 44 17 719 | 11/1995 | Germany . |

OTHER PUBLICATIONS

Schlaefer et al. EP 535495—Water–soluble azo compounds . . . CAPLUS Abstract Provided, 1994.

Ohme et al. DD 299416—Preparation of pyrrolidinium sulfobetaines . . . CAPLUS abstract provided, 1992.

K. Venkataraman, "The Chemistry of Synthetic Dyes", vol. 6, Academic Press, New York, London. 1972 pp 201–208.

*Primary Examiner*—Richard L. Raymond
*Assistant Examiner*—Venkataraman Balasubramanian
*Attorney, Agent, or Firm*—Oblon, Spivak, McClelland, Maier & Neustadt, P.C.

[57] ABSTRACT

Amino- and/or alkoxytriazines containing at least one $C_1$–$C_{10}$-alkyl group which possesses a vinylsulfonyl group or a radical capable of forming a vinylsulfonyl group and may be substituted further, are used as fixation aids when using anionic dyes on hydroxyl- or nitrogen-containing organic substrates and as crosslinkers for regenerated cellulose or materials containing cellulose.

9 Claims, No Drawings

TRIAZINE DERIVATIVES AS FIXERS IN COLORING AND AS CROSS-LINKING AGENTS

DESCRIPTION

The present invention relates to novel triazine derivatives of the formula I:

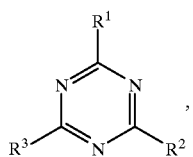

(I)

where $R^1$ is $NL^1L^2$ or $OL^1$;
$R^2$ is $NL^1L^2$ or $OL^1$ or halogen;
$R^3$ is $NL^1L^2$, $OL^1$, $C_1$–$C_4$-alkyl or phenyl, which may be substituted once or twice by hydroxysulfonyl, chlorine, nitro, $C_1$–$C_4$-alkyl, $C_1$–$C_4$-alkoxy, cyano, carboxyl, acetylamino, hydroxysulfonylmethyl or $CH_2$—$SO_2$—Y, $SO_2$—Y, $NL^1$—CO—Y or $NL^1$—CO—$NL^1$—Z—$SO_2$—Y;

$L^1$ is hydrogen or $C_1$–$C_{10}$-alkyl which can be substituted with —$SO_2$—Y and which is uninterrupted or interrupted each time by 1–3 oxygens in ether function or by nonadjacent iminos or $C_1$–$C_4$-alkyliminos;

$L^2$ is $L^1$ or phenyl which can be substituted once or twice with hydroxysulfonyl, chlorine, nitro, $C_1$–$C_4$-alkyl, $C_1$–$C_4$-alkoxy, cyano, carboxyl, acetylamino, hydroxysulfonylmethyl or $CH_2$—$SO_2$—Y, $SO_2$—Y, $NL^1$—CO—Y, CO—$NL^1$-Z—$SO_2$—Y or $NL^1$—CO—$NL^1$—Z—$SO_2$—Y, or $L^1$ and $L^2$, together with the nitrogen linking them, are pyrrolidinyl, piperidinyl, morpholinyl, piperazinyl or N—($C_1$–$C_4$-alkyl) piperazinyl;

Z is $C_2$–$C_6$-alkylene which is unsubstituted or substituted by hydroxyl, chlorine, cyano, carboxyl, $C_1$–$C_4$-alkoxycarbonyl, $C_1$–$C_4$-alkanoyloxy or sulfato and may be interrupted each time by 1 or 2 oxygens in ether function or by nonadjacent iminos or $C_1$–$C_4$-alkyliminos;

Y is vinyl or $C_2H_4$—Q in which Q is an alkali-eliminable group;

with the proviso that in $R^1$ $L^1$ is $C_1$–$C_{10}$-alkyl substituted with —$SO_2$—Y and is uninterrupted or interrupted each time by 1–3 oxygens in ether function or by nonadjacent iminos or $C_1$–$C_4$-alkyl-iminos, and to their use as fixation aids when using anionic dyes to dye hydroxyl- or nitrogen-containing organic substrates and as cross-linkers for regenerated cellulose or materials containing cellulose.

K. Venkataraman in The Chemistry of Synthetic Dyes, Volume 6, Academic Press, New York, London, 1972, pp 201 to 208 discloses fixation aids for dyeing with anionic dyes.

However, it has been found that the compounds described therein do not yet fully live up to expectations.

It is an object of the present invention, therefore, to provide novel triazine derivatives advantageously suitable for employment as fixation aids when using anionic dyes to dye hydroxyl- or nitrogen-containing organic substrates and as crosslinkers for regenerated cellulose.

We have found that this object is achieved by the above-defined triazine derivatives of the formula I.

Where the novel triazine derivatives of the formula I carry hydroxysulfonyls or carboxyls, then the claims of course embrace their salts as well.

Suitable cations are metal ions or ammonium ions, the former being, in particular, lithium, sodium and potassium ions and the latter referring for the purposes of the invention to unsubstituted or substituted ammonium cations. Examples of substituted ammonium cations are monoalkyl-, dialkyl-, trialkyl-, tetraalkyl- and benzyltrialkylammonium cations, or those cations derived from five- or six-membered saturated heterocycles containing nitrogen, such as pyrrolidinium, piperidinium, morpholinium or piperazinium cations or their N-monoalkyl- or N,N-dialkyl-substituted counter-parts. Alkyl here generally means straight-chain or branched $C_1$–$C_{20}$-alkyl which may be substituted by 1 or 2 hydroxyls and/or interrupted by 1–4 oxygens in ether function.

Any alkyl or alkylene mentioned in this application can be either straight-chain or branched.

Substituted alkyls or alkylenes in this application generally have 1 or 2 substituents.

For the purposes of the present invention, halogen is fluorine or chlorine.

Q is an alkali-eliminable group, i.e. one which can be eliminated under alkaline reaction conditions, examples being chloro, bromo, $C_1$–$C_4$-alkylsulfonyl, phenylsulfonyl, $OSO_3H$, $SSO_3H$, $OP(O)(OH)_2$, $C_1$–$C_4$-alkylsulfonyloxy, phenylsulfonyloxy, $C_1$–$C_4$-alkanoyloxy, $C_1$–$C_4$-dialkylamino or:

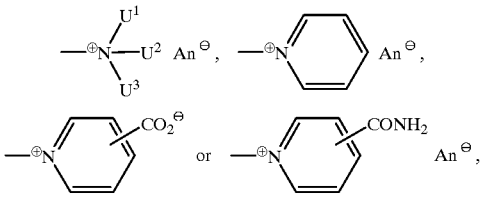

where $U^1$, $U^2$ and $U^3$ independently are each $C_1$–$C_4$-alkyl or benzyl and $An^-$ is one equivalent of an anion. Examples of suitable anions in this context are fluoride, chloride, bromide, iodide and mono-, di- or trichloroacetate, methanesulfonate, benzenesulfonate and 2- or 4-methylbenzenesulfonate.

Any alkyls or alkylenes in the formulae above that are interrupted by oxygens in ether function or by iminos or $C_1$–$C_4$-alkyliminos are preferably interrupted by 1 or 2 oxygens in ether function or by iminos or $C_1$–$C_4$-alkyliminos.

Examples of $L^1$, $L^2$ and $R^3$ are methyl, ethyl, propyl, isopropyl, butyl, isobutyl, sec-butyl or tert-butyl.

Further examples of $L^1$ and $L^2$ are pentyl, isopentyl, neopentyl, tert-pentyl, hexyl, 2-methylpentyl, heptyl, octyl, 2-ethylhexyl, isooctyl, nonyl, isononyl, decyl, isodecyl [isooctyl, isononyl and isodecyl are trivial names arising from the alcohols obtained by oxo synthesis (cf. Ullmann's Encyclopedia of Industrial Chemistry, 5th Edition, Vol. Al, pp. 290–293, and Vol. A 10, pp. 284 and 285)], 2-methoxyethyl, 2-ethoxyethyl, 2-propoxyethyl, 2-butoxyethyl, 2- or 3-methoxypropyl, 2- or 3-ethoxypropyl, 2- or 3-propoxypropyl, 2- or 4-methoxybutyl, 2- or 4-ethoxybutyl, 3,6-dioxaheptyl, 3,6-dioxaoctyl, 3,7-dioxaoctyl, 4,7-dioxaoctyl, 2- or 3-butoxypropyl, 2- or 4-butoxybutyl, 4,8-dioxanonyl, 3,7-dioxanonyl, 4,7-dioxanonyl, 4,8-dioxadecyl, 3,6,9-trioxadecyl, 3,6,9-trioxaundecyl, 2-methylaminoethyl, 2-dimethylaminoethyl, 2-ethylaminoethyl, 2-diethylaminoethyl, 2- or 3-methylaminopropyl, 2- or 3-dimethylaminopropyl, 2- or 3-ethylaminopropyl, 2- or 3-diethylaminopropyl, 2- or 4-methylaminobutyl, 2- or 4-dimethylaminobutyl, 2- or 4-ethylaminobutyl, 2- or 4-di-ethylaminobutyl, $C_2H_4$—$SO_2$—Y, $C_3H_6$—$SO_2$—Y, $C_4H_8$—$SO_2$—Y, $C_2H_4OC_2H_4$—$SO_2$—Y, $C_2H_4$—NH—$C_2H_4$—$SO_2$—Y, $C_2H_4$—N($CH_3$)—$C_2H_4$—$SO_2$—Y, $C_2H_4OC_2H_4OC_2H_4$—$SO_2$—Y, $C_2H_4$—NH—$C_2H_4$—NH—$C_2H_4$—$SO_2$—Y or $C_2H_4$—N($CH_3$)—$C_2H_4$—N($CH_3$)—$C_2H_4$—$SO_2$—Y.

Examples of Z are $CH_2$, $(CH_2)_2$, $(CH_2)_3$, $(CH_2)_4$, $(CH_2)_5$, $(CH_2)_6$, $CH(CH_3)CH_2$, $CH(CH_3)CH(CH_3)$, $C_2H_4$—O—$C_2H_4$, $C_2H_4$—NH—$C_2H_4$, $C_2H_4N(CH_3)$—$C_2H_4$, $C_2H_4$—O—$C_2H_4$—O—$C_2H_4$, $C_2H_4$—NH—$C_2H_4$—NH—$C_2H_4$, $C_2H_4$—N($CH_3$)—$C_2H_4$—N($CH_3$)—$C_2H_4$ or $C_2H_4$—O—$C_2H_4$—N($CH_3$)—$C_2H_4$.

$R^3$ and further $L^2$ are phenyl, 2-, 3- or 4-hydroxysulfonylphenyl, 2-, 3- or 4-chlorophenyl, 2-, 3- or 4-nitrophenyl, 2-, 3- or 4-methylphenyl, 2-, 3- or 4-methoxyphenyl, 2-, 3- or 4-cyanophenyl, 2-, 3- or 4-carboxyphenyl, 2-, 3- or 4-acetylaminophenyl, 2-, 3- or 4-hydroxysulfonylmethylphenyl,

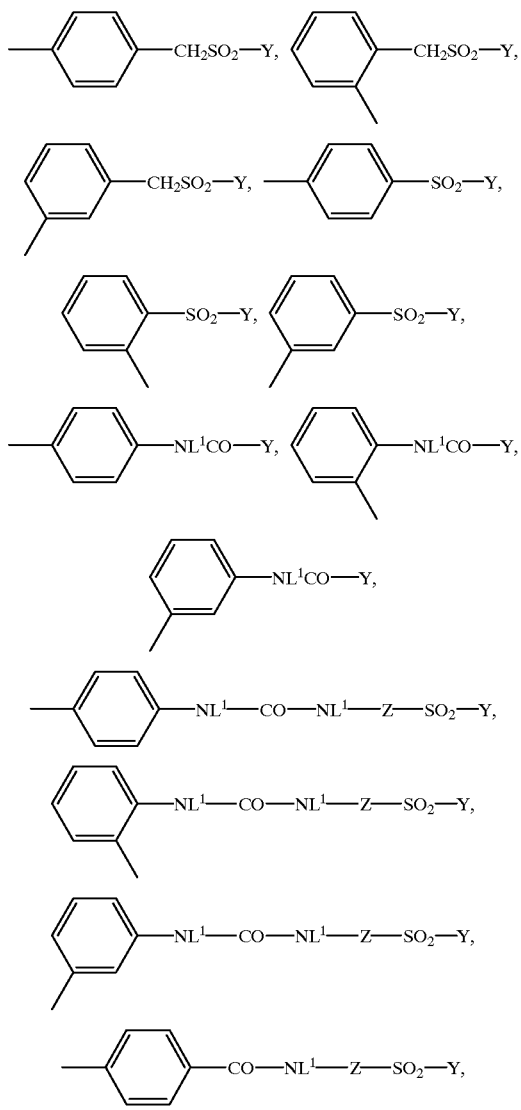

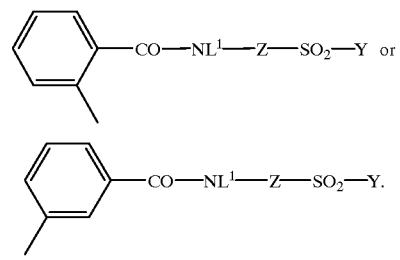

Where $NL^1L^2$ occurs more than once in formula I, the radicals can be different from one another. The same applies to $OL^1$. Preference is given to compounds of the formula I in which the $NL^1L^2$s and $OL^1$s are identical.

Furthermore, two or more radicals $L^1$, for example in $R^3$, are mutually independent.

Preferred triazine derivatives (of the formula) I are those in which $R^1$, $R^2$ and $R^3$ are mutually independent and are $NL^1L^2$.

Further preferred triazine derivatives I are those in which $L^1$ and $L^2$ independently are each hydrogen, $C_1$–$C_4$-alkyl or $C_1$–$C_{10}$-alkyl which is substituted with —$SO_2$—Y and is uninterrupted or interrupted each time by 1–3 oxygens in ether function or by nonadjacent iminos or $C_1$–$C_4$-alkyliminos.

Other preferred triazine derivatives I are those in which Y is vinyl, 2-sulfatoethyl, 2-chloroethyl or 2-acetyloxyethyl.

Particularly preferred triazine derivatives I are those in which $L^1$ and $L^2$ independently are each hydrogen or $C_1$–$C_8$-alkyl which is substituted with —$SO_2$—Y and is uninterrupted or interrupted each time by 1 or 2 oxygens in ether function or by nonadjacent iminos or $C_1$–$C_4$-alkyliminos.

Especially preferred triazine derivatives I are those in which $L^1$ is hydrogen or $C_1$–$C_6$-alkyl which is substituted with —$SO_2$—Y and is uninterrupted or interrupted by an oxygen in ether function or by an imino or $C_1$–$C_4$-alkylimino, and $L^2$ is hydrogen.

Particular interest attaches to triazine derivatives of the formula Ia:

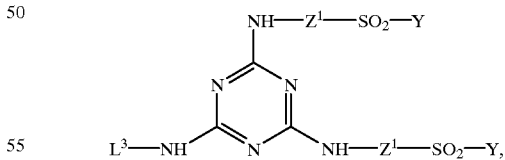

(Ia)

where $Z^1$ is $C_2$–$C_6$-alkylene which is uninterrupted or interrupted by an oxygen in ether function, and $L^3$ is hydrogen or $Z^1$—$SO_2$—Y, and Y is as defined above.

The novel triazine derivatives I can be obtained conventionally, for example by reacting cyanuric halides of the formula II:

$$\text{(II)}$$

[Structure: triazine ring with Hal at top, R⁴ and Hal on bottom positions]

where Hal is halogen, especially chlorine, and $R^4$ is halogen, especially chlorine, $C_1$–$C_4$-alkyl or phenyl which can be substituted once or twice by hydroxysulfonyl, chlorine, nitro, $C_1$–$C_4$-alkyl, $C_1$–$C_4$-alkoxy, cyano, carboxyl, acetylamino, hydroxysulfonylmethyl or $CH_2$—$SO_2$—Y, $SO_2$—Y, $NL^1$—CO—Y or $NL^1$—CO—$NL^1$—Z—$SO_2$—Y, with amines of the formula III and/or hydroxy compounds of the formula IV:

| $NHL^1L^2$ | $L^1OH$ |
|---|---|
| (III) | (IV), | in which $L^1$ and $L^2$ are each as defined above.

Another option is to react amino triazines of the formula V:

$$\text{(V)}$$

[Structure: triazine ring with NH₂ at top, R⁵ and NH₂ on bottom positions]

where $R^5$ is amino, $C_1$–$C_4$-alkyl or phenyl, which may be substituted once or twice by hydroxysulfonyl, chlorine, nitro, $C_1$–$C_4$-alkyl, $C_1$–$C_4$-alkoxy, cyano, carboxyl, acetylamino, hydroxysulfonylmethyl or $CH_2$—$SO_2$—Y, $SO_2$—Y, $NL^1$—CO—Y or $NL^1$—CO—$NL^1$—Z—$SO_2$—Y, with amines of the formula III and/or hydroxy compounds of the formula IV, during which ammonia is given off.

The novel triazine derivatives are advantageously suitable as fixation aids when using anionic dyes to dye hydroxyl- or nitrogen-containing organic substrates.

Examples of suitable subtrates are leather or fiber material composed predominantly of natural or synthetic polyamides or of natural or regenerated cellulose. Keratinous fibers such as hairs and skins are also suitable. The textile material is preferably based on wool or, in particular, on cotton.

Examples of suitable anionic dyes are those carrying one or more hydroxysulfonyls, aminosulfonyls and/or carboxyls. They may also carry one or more fiber-reactive groups as well.

For example, they come from the class of monoazo or polyazo dyes, metallized formazan dyes, for example copper formazan dyes, anthraquinone dyes, triphendioxazine dyes or phthalocyanine dyes.

In place of the azo dyes, the corresponding metal complex azo dyes may also be employed, in which case particularly suitable complexing metals are copper, cobalt, chromium, nickel or iron, preferably copper, cobalt or chromium.

In such dyes the metallized groups are preferably each ortho to the azo group, for example as o,o'-dihydroxy-azo-, o-hydroxy-o'-carboxyl-azo-, o-carboxyl-o'-amino-azo or o-hydroxy-o'-amino-azo groups.

The abovementioned dyes are generally known and commercially available and are described, for example, in the Colour Index under Acid Dyes or Reactive Dyes.

The mode of action of the fixation aids is known and is described, for example, in K. Venkataraman (loc. cit.). This involves dyes carrying a nucleophilic group being attached by means of the fixation aids to the hydroxyl- or nitrogen-containing organic substrates.

One example of a special option for using the novel triazine derivatives as fixation aids is to employ them directly in ready-to-use preparations together with the anionic dye. Such preparations may, for example, be in the form of powders or granules which can be obtained by combined spray-drying of the synthesis solutions of triazine derivative and anionic dye.

The novel triazine derivatives are also suitable as crosslinkers for regenerated cellulose or cellulose-containing materials, as described in EP-A 538 977, for example.

Triazine derivatives I having at least two fiber-reactive groups in the molecule are also useful as the fiber-reactive moiety of reactive dyes.

The examples which follow are intended to illustrate the invention.

EXAMPLE 1 a) 37.5 g of concentrated sulfuric acid were added dropwise with stirring to a mixture of 229 g of melamine and 1530 g of 2,2'-aminoethoxyethanol. The mixture was then stirred at 210–220° C. for 11 h with a weak stream of nitrogen being passed over it.

After the mixture had cooled, 58.3 g of 50% strength by weight sodium hydroxide solution were added and the precipitated sodium sulfate was removed by filtration. Subsequently, excess 2,2'-aminoethoxyethanol was removed by distillation under reduced pressure, giving 702 g of N,N',N"-tris(5-hydroxy-3-oxapentyl)melamine as a yellowish resin, purity: 96–98% (HPLC)

b) 296 g of the compound described in a) were introduced at room temperature into 600 g of thionyl chloride. After the exothermic reaction had subsided, the mixture was heated at 60–70° C. for 3 h and subsequently allowed to cool. The product was precipitated by adding 2000 g of petroleum ether. Filtration with suction was followed by drying, and 243 g of N,N',N" tris(5-chloro-3-oxapentyl)melamine were isolated.

c) 270 g of 30% strength by weight methanolic sodium methanolate solution and 94 g of 2-mercaptoethanol in 300 g of n-butanol were heated at 115 to 118° C. After the distillation of methanol was over, 135 g of the compound described in b) were added the mixture was refluxed for 3 h and subsequently allowed to cool. 1000 ml of water were added and the organic phase was separated off. Following distillative removal of the n-butanol, 135 g of the compound of the formula:

[Structure: triazine ring with A¹ at each of three positions]

$(A^1 = NHC_2H_4OC_2H_4SC_2H_4OH)$ were isolated as a pale brown oil.

d) A mixture of 45.6 g of the compound described in c), 3.5 g of acetic acid, 0.5 g of tungstic acid and 150 ml of water was subjected to the dropwise addition at 60° C. of 57 g of 30% strength by weight hydrogen peroxide, giving rise to a highly exothermic reaction. After 3 h at 85° C., peroxide could no longer be detected. The solvent was removed by distillation under reduced pressure to give 55 g of the compound of the formula:

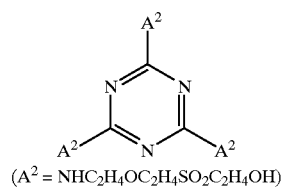

($A^2$ = $NHC_2H_4OC_2H_4SO_2C_2H_4OH$)

as a brownish resin.

e) 107 g of the compound described in d) were introduced slowly into 500 g of pure sulfuric acid at a rate such that the temperature did not exceed 25° C. After 10 h the homogeneous solution was poured onto 3000 g of ice and the pH was adjusted to 4.5 using solid calcium carbonate. The mixture was filtered with suction and the filtrate was concentrated under reduced pressure at <30° C. The residue was 165 g of a brown resin which showed a molar peak in the mass spectrum (electrospray ionization) at 906 and corresponds to the formula:

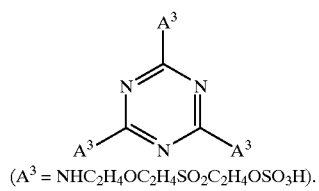

($A^3$ = $NHC_2H_4OC_2H_4SO_2C_2H_4OSO_3H$).

EXAMPLE 2 a) 97 g of 2-hydroxyethyl-2'-aminoethyl sulfide were added dropwise to 46 g of cyanuric chloride and 69 g of anhydrous potassium carbonate in 1000 g of dioxane. The reaction mixture was refluxed for 7 h with a weak stream of nitrogen being passed over it.

The reaction mixture was cooled and filtered and the filtrate was concentrated by evaporation to give a yellow oil which was purified by chromatography on silica gel using isopropanol. The initial fraction eluted was N,N',N"-tris(5-hydroxy-3-thiapentyl)melamine, in a yield of 88 g of yellowish resin.

b) A mixture of 294 g of the compound described in a), 50 g of acetic acid, 2 g of tungstic acid and 600 ml of water was subjected at 80–85° C. to the dropwise addition of 453 g of 30% strength by weight hydrogen peroxide. After 2 h more at 80–85° C., the mixture was filtered and the filtrate was concentrated under reduced pressure to give 350 g of the compound of the formula:

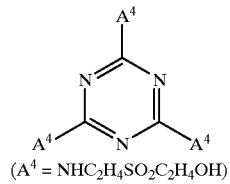

($A^4$ = $NHC_2H_4SO_2C_2H_4OH$)

c) 81 g of the compound described in b) were introduced at <25° C. into 700 g of 5% strength by weight oleum. After 10 h, the mixture was poured onto 3500 g of ice and the pH was adjusted to 5.5 by adding calcium carbonate. The mixture was filtered with suction and the mother liquor was spray-dried to give 70 g of a pale yellowish, readily water-soluble powder (m.p. <300° C.) whose mass spectrum (electrospray ionization) is in accordance with the formula:

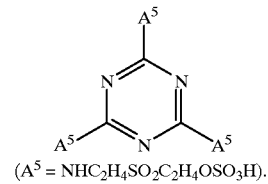

($A^5$ = $NHC_2H_4SO_2C_2H_4OSO_3H$).

EXAMPLE 3 (Use)

Woven cotton fabric is impregnated on a two-roll padder at room temperature with a liquor which in 1000 parts by weight of water comprises 40 parts by weight of the dye of the formula:

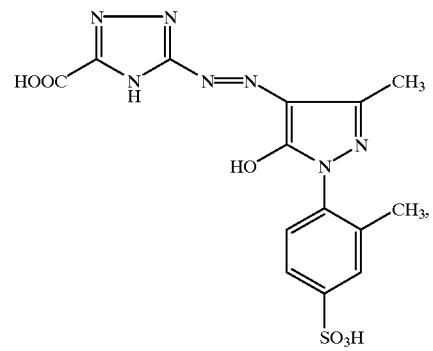

40 parts by weight of the triazine derivative described in Example 2c and 20 parts by weight of 32% strength by weight sodium hydroxide solution. The fabric is squeezed off to a pick-up of 70%, dried initially at 80° C. and then steamed at 102° C. for 8 minutes. It is then rinsed and soaped at the boil to give a deep, greenish-yellow dyeing with outstanding manufacturing and in-use fastness properties, in particular very good light fastness and wash fastness.

EXAMPLE 4 (Use)

Woven cotton fabric is impregnated on a two-roll padder at room temperature with a liquor which in 1000 parts by weight of water comprises 80 parts by weight of the dye of the formula:

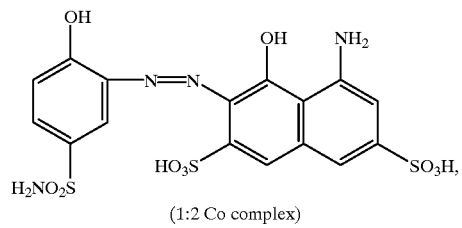

(1:2 Co complex)

parts by weight of the triazine derivative described in Example 2c, 20 parts by weight of 32% strength by weight sodium hydroxide solution and 50 parts by weight of sodium silicate (38° Bé). The fabric is squeezed off to a pick-up of 70%, rolled up, wrapped with a film and then stored wet at room temperature for 24 h. It is then rinsed and soaped at the boil to give a deep, gray dyeing with outstanding manufacturing and in-use fastness properties.

EXAMPLE 5 (Use)

100 g of skin pelt are dyed in a bath containing 5000 parts by weight of water, 5 parts by weight of the dye of the formula:

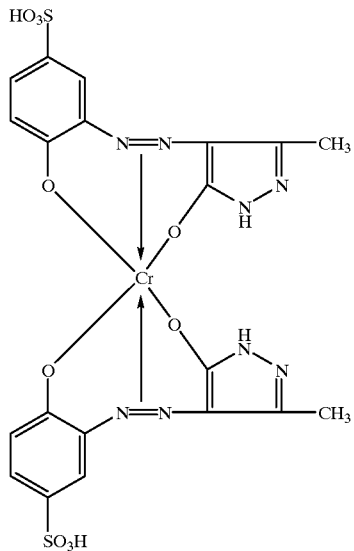

and 5 parts by weight of the triazine derivative described in Example 2c at a pH of 3.5 (established using 10% strength by weight acetic acid).

Dyeing is commenced at room temperature after which the bath is raised over the course of 20 minutes to 60° C., at which dyeing is continued for 40 minutes. The pH of the dyebath is then adjusted to 8.0 by adding 25% strength by weight ammonia solution, and dyeing is continued at this pH and at 60° C. for 20 minutes.

After rinsing, first of all in hot water at 50° C. and then in cold water, an orange-colored skin-pelt dyeing with good fastness properties is obtained.

We claim:

1. A triazine compound of the formula I:

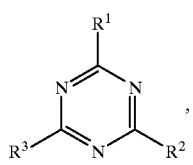

where $R^1$ is $NL^3L^2$ or $OL^3$;

$R^2$ is $NL^1L^2$ or $OL^1$ or halogen;

$R^3$ is $NL^1L^2$, $C_1$–$C_{10}$-alkoxy substituted with —$SO_2$—Y and which is uninterrupted or interrupted each time by 1–3 oxygens in ether function or by nonadjacent iminos or $C_1$–$C_4$-alkyliminos, $C_1$–$C_4$-alkyl or $R^3$ is phenyl, which may be substituted once or twice by hydroxysulfonyl, chloride, nitro, $C_1$–$C_4$-alkyl, $C_1$–$C_4$-alkoxy, cyano, carboxyl, acetylamino, hydroxysulfonylmethyl or $CH_2$—$SO_2$—Y, $SO_2$—Y, $NL^1$—CO—Y or $NL^1$—CO-$NL^1$—Z—$SO_2$—Y;

$L^1$ is hydrogen or $C_1$–$C_{10}$-alkyl which can be substituted with —$SO_2$—Y and which is uninterrupted or interrupted each time by 1–3 oxygens in ether function or by nonadjacent iminos or $C_1$–$C_4$-alkyliminos;

$L^2$ is $L^1$ or $L^2$ is phenyl which can be substituted once or twice with hydroxysulfonyl, chloride, nitro, $C_1$–$C_4$-alkyl, $C_1$–$C_4$-alkoxy, cyano, carboxyl, acetylamino, hydroxysulfonylmethyl or $CH_2$—$SO_2$—Y, $SO_2$—Y, $NL^1$—CO—Y, CO—$NL^1$—Z—$SO_2$—Y or $NL^1$—CO—$NL^1$—Z—$SO_2$—Y, or $L^1$ and $L^2$, together with the nitrogen linking them, are pyrrolidinyl, piperidinyl, morpholinyl, piperazinyl, or N—($C_1$–$C_4$-alkyl) piperazinyl;

Z is $C_2$–$C_6$-alkylene which is unsubstituted or substituted with hydroxyl, chlorine, cyano, carboxyl, $C_1$–$C_4$-alkoxycarbonyl, $C_1$–$C_4$-alkanoyloxy or sulfato and may be interrupted each time by 1 or 2 oxygens in ether function or by nonadjacent iminos or $C_1$–$C_4$-alkyliminos;

Y is vinyl or $C_2H_4$—Q in which Q is an alkali-eliminable group; and $L^3$ is $C_1$–$C_{10}$-alkyl substituted with —$SO_2$—Y and is uninterrupted or interrupted each time by 1–3 oxygens in ether function or by nonadjacent iminos or $C_1$–$C_4$-alkyliminos, the alkali-eliminable group Q being a group eliminable when the triazine is employed in dyeing with a dyeing mixture under alkaline mixtures.

2. A triazine derivative as claimed in claim 1, wherein $R^1$ is $NL^3L^2$ and $R^2$ and $R^3$ are mutually independent and are $NL^1L^2$.

3. A triazine derivative as claimed in claim 1, wherein $L^1$ and $L^2$ independently are each hydrogen, $C_1$–$C_4$-alkyl or $C_1$–$C_{10}$-alkyl which is substituted with —$SO_2$—Y and is uninterrupted or interrupted each time by 1–3 oxygens in ether function or by nonadjacent iminos or $C_1$–$C_4$-alkyliminos.

4. A triazine derivative as claimed in claim 1, wherein $L^1$ and $L^2$ independently are each hydrogen or $C_1$–$C_8$-alkyl which is substituted with —$SO_2$—Y and is uninterrupted or interrupted each time by 1 or 2 oxygens in ether function or by nonadjacent iminos or $C_1$–$C_4$-alkyliminos.

5. A triazine derivative as claimed in claim 1, wherein $L^1$ is hydrogen or $C_2$–$C_6$-alkyl which is substituted with $SO_2$—Y and is uninterrupted or interrupted by an oxygen in ether function or by an imino or $C_1$–$C_4$-alkylimino, and $L^2$ is hydrogen.

6. The process of applying a triazine compound as claimed in claim 1 as a fixation aid and an anionic dye to hydroxyl- or nitrogen-containing organic substrate to dye them.

7. The process of applying a triazine compound as claimed in claim 1 to regenerated cellulose or to materials containing regenerated cellulose as a crosslinker for the regeneration cellulose or the materials containing cellulose.

8. A triazine derivative as claimed in claim 1 wherein $R^1$, $R^2$ and $R^3$ are each $NHC_2H_4OC_2H_4SO_2C_2H_4OSO_3H$.

9. A triazine derivative as claimed in claim 1 wherein $R^1$, $R^2$ and $R^3$ are each $NHC_2H_4SO_2C_2H_4OSO_3H$.

* * * * *